United States Patent [19]

Heimburger et al.

[11] 4,178,368
[45] Dec. 11, 1979

[54] METHOD FOR THE TREATMENT OF THROMBOEMBOLISM

[75] Inventors: Norbert Heimburger; Hansjörg Ronneberger; Manfred Schick, all of Frankfurt am Main, Fed. Rep. of Germany

[73] Assignee: Behringwerke Aktiengesellschaft, Marburg an der Lahn, Fed. Rep. of Germany

[21] Appl. No.: 917,583

[22] Filed: Jun. 21, 1978

Related U.S. Application Data

[63] Continuation-in-part of Ser. No. 850,808, Nov. 11, 1977, abandoned, which is a continuation of Ser. No. 736,831, Oct. 29, 1976, abandoned, which is a continuation of Ser. No. 293,213, Sep. 28, 1972, abandoned.

[30] Foreign Application Priority Data

Sep. 30, 1971 [DE] Fed. Rep. of Germany ....... 2148865

[51] Int. Cl.$^2$ ............................................. A61K 37/48
[52] U.S. Cl. ........................................................ 424/94
[58] Field of Search .......................................... 424/94

[56] References Cited

PUBLICATIONS

Kline, Yale Journal of Biol & Med., vol. 26 (1954), pp. 365–371.
Ionesco-Stoian et al., Rev. Jour. Biochem., 6(2), pp. 135–145 (1969).

Primary Examiner—Stanley J. Friedman
Attorney, Agent, or Firm—Curtis, Morris & Safford

[57] ABSTRACT

A method for the treatment of thromboembolisms in a patient, said method consisting essentially of intravenously administering to said patient an effective amount of a complex formed between streptokinase and plasminogen in a mol ratio from 2:1 to 1:2 in combination with a physiologically tolerable aqueous liquid diluent.

2 Claims, No Drawings

METHOD FOR THE TREATMENT OF THROMBOEMBOLISM

The present invention relates to a method for the treatment of thromboembolisms. This application is a continuation-in-part application of application Ser. No. 850,808 filed Nov. 11, 1977, by Norbert Heimburger and Hansjörg Ronneberger for FIBRINOLYSIS ACTIVATOR AND PROCESS FOR ITS MANUFACTURE, which is a continuation application of application Ser. No. 736,831, filed Oct. 29, 1976, which, in turn, is a continuation of application Ser. No. 293,213 filed Sept. 28, 1972 by the same inventors for FIBRINOLYSIS ACTIVATOR AND PROCESS FOR ITS MANUFACTURE, all are now abandoned.

Under the action of streptokinase, which is a metabolism product of β-hemolyzing streptococci, plasminogen of the blood is converted into the protease plasmin which is capable of dissolving fibrin clots and which is therefore used on a clinical scale for starting fibrinolysis. As an ectogenic substance, streptokinase has the property of forming antibodies in a macroorganism; it can therefore not be administered repeatedly to patients without causing side reactions. Attempts have already been made to obtain streptokinase of reduced antigenicity by treating it with proteolytic enzymes. However, even the residual antigenicity of a so-treated streptokinase may lead to undesired reactions in sick persons.

The present invention provides a fibrinolysis activator which comprises an injectible solution of streptokinase and human plasminogen in a ratio of 2:1 to 1:2 and, furthermore, the treatment of a patient suffering from thromboembolism with such injectible solution by intravenous injection.

For the manufacture of this fibrinolysis activator containing streptokinase, an aqueous solution of streptokinase is mixed with human plasminogen in a molar ratio of 2:1 to 1:2, preferably of 1:1, the molecular weight of human plasminogen being about 84,000 and that of streptokinase about 47,000.

Streptokinase and human plasminogen enter into a more or less strong chemical linkage with each other, depending on the conditions under which they are mixed. The compound can be dissociated by means of ε-aminocaproic acid if the reaction is carried out in the cold. If heat is applied, stronger agents, for example urea, have to be used to bring about dissociation. It can be presumed that a chemical reaction takes place on heating since a treatment of the reaction product with urea releases an altered streptokinase characterized, for example, by a reduced electrophoretical mobility.

Streptokinase and plasminogen are known products. It is surprising and was not known in the art that human plasminogen masks the antigenous groups of streptokinase against the human organism and obviates the risk involved in the intravenous injection of streptokinase, which, in many cases, may save life.

The preparation of the invention is suitable for the treatment of thrombo-embolic diseases and is effective even if the patient has antibodies against streptokinase due to a previous contact with streptococci or to a preceding injection of streptokinase.

The streptokinase linked with plasminogen is hardly affected by the homologous antibody. This finding can be evidenced by preparing several mixtures of constant amounts of streptokinase with increasing amounts of human plasminogen and by adding equal amounts of the homologous antibody to these mixtures having a different plasminogen content. Thus, increasing amounts of plasminogen reduce the precipitability of streptokinase by the antibody.

Alternatively, streptokinase may be released from its linkage with plasminogen by means of ε-amino-caproic acid and then it reacts again, without limitation, with its homologous antibody.

When immunized with streptokinase, guinea pigs produce antibodies against streptokinase. An injection of streptokinase made after three weeks, therefore, brings about a shock reaction. If, however, the streptokinase-plasminogen complex compound is injected to guinea pigs after three weeks, this injection is tolerated without causing a reaction.

Guinea pigs immunized with the streptokinase-plasminogen activator of the invention do not produce antibodies against streptokinase, but they produce antibodies against human plasminogen. After three weeks, the animals thus immunized tolerate an injection of streptokinase without complication, but they react upon a boostering with the activator of the invention by showing allergy or anaphylaxy symptoms due to the human plasminogen antibodies present.

Another advantage of the preparation of the invention is that it remains unaffected by the natural inhibitors of the blood. Thus, it can easily penetrate to the blood clot and dissolve it. There are no preliminary tests required and the preparation can be administered in uniform dosage units.

The dosage in which the complex is administered to a human patient is at least 50,000 u per hour. In some cases this dosage will prove to be to low to cause a satisfactory effect. Higher dosages which—in case of a resistance to streptokinase—may range up to 1,000,000 units per hour are then required. The optimum treatment will be achieved by an initial dosage of about 250,000 units administered in about 20 minutes and followed by a continuous treatment with about 100,000 units per hour, over several hours, if desired up to some days.

The complex is administered in combination with a physiologically tolerable aqueous liquid diluent. Such diluent contains in an aqueous solution an amount of physiologically tolerable salts sufficient to render it isotonic with normal human blood plasma. Preferably a so-called physiological sodium chloride solution, i.e. a 0.9% aqueous solution of sodium chloride is used as the diluent. Instead of sodium chloride, the diluent may contain in part or in whole other physiologically tolerable salts and, in addition, if desired, further ingredients such as glucose or a known stabilizer.

Clinical and Laboratory Findings

Five patients were treated with the activator, i.e. an equimolar complex of streptokinase and human plasminogen. The activator quantity infused in 1 hour was 100,000 u dissolved in 3.75 ml physiological NaCl solution.

100,000 u of activator was analyzed and shown to consist of 132,000 u of streptokinase (SK) plus the plasminogen equivalent of 29 ml human standard plasma. Furthermore, the activity of 100,000 u of activator was equal to 453,000 CTA-u of urokinase.

The activator solution was given by an infusion pump. As mentioned before, the hourly influx was 3.75 ml containing 100,000 u of activator. The loading dose was calculated according to the circulating anti-SK content (CAC), tiltrated according to the method of DEUTSCH and FISCHER Thromb. Diath. haemmorh 4,482 (1960). For example, if a CAC of 50,000 anti-SK u was determined, a loading dose of 50,000 u of activator was infused over 20 minutes. Every 12 hours a newly prepared activator solution was provided.

There was a considerable decay in activator concentration during the 12-hour infusion period. The activator loss averaged 59%, the SK component fell by 51%, and the decrease in plasminogen component was 40%.

Activator treatment was performed in 4 patients. The targets of treatment were 4 iliac narrowings. Clinical monitoring was provided by post-stenotic pressure measurements according to the ultrasonic technique, as well as by oscillography at rest and after exercise. Laboratory controls were conducted by measurement of prothrombin time, plasma thrombin time, fibrinogen, plasminogen, plasmin, and activator concentrations (SKAPP concentrations). Plasma samples were drawn before treatment and 1, 2, 4, 6, 24, 48 and 75 h after starting therapy.

Activator infusion was accompanied by a decrease of plasminogen to values around 20 and 30%. Plasmin quantities rose in a reciprocal manner, i.e. a peak of 0.02 novo-u/ml of plasma was recorded 1 hour after starting treatment and an average concentration of 0.012 novo-u/ml of plasma during the subsequent period of time. Fibrinogen fell moderately from 400 mg% before therapy to an average of 150 mg% at the end of treatment. Directly after start of activator infusion a shortening of partial thromboplastin times was recorded, indicating a transient hypercoagulability, a phenomenon regularly seen at the beginning of various forms of SK treatment. Thereafter, PTT values increased and averaged 45 sec (normal 40 sec). A prolongation of the plasma thrombin times up to an average of 65 sec (normal 20 sec) was additionally produced.

Interestingly, no measurable activator or streptokinase activity appeared in the plasma during therapy. This observation was contradictory to findings seen in the conventional SK regimens.

Clinical details of the 4 patients are compiled in Table 1

A further activator treatment was performed on a patient displaying a right femoral stenosis, a left iliac stenosis and additionally, a left femoral occlusion of half a year's standing. 1 day after start of treatment an increase in ankle pressure by 20 mm Hg was recorded in the right leg, indicating the widening of the right femoral narrowing. 2 days after start of treatment a quite dramatic ankle pressure elevation by 70 mm Hg occurred in the left side. Clinical examination as well as oscillographic recordings showed the removal of the left femoral occlusion. This assumption was proven by the check-up angiogram. With this it became evident that all three obstructions (right femoral and left iliac stenoses, left femoral occlusion) had been removed.

Checking the fibrinolytic and coagulation data, a moderately decreased plasminogen concentration and a measureable plasmin activity were found during the whole course of activator infusion. As in the foregoing cases, neither activator nor streptokinase quantities were traceable.

The following Example serves to illustrate the invention.

EXAMPLE

A 2% solution of streptokinase in a physiological sodium chloride solution and a 1% solution of human plasminogen in a 0.1 molar sodium phosphate buffer were mixed in an ice bath in the following batches, streptokinase being present in a constant amount and plasminogen being added in increasing amounts.

(1) 0.1 ml of streptokinase+0.9 ml of physiological sodium chloride solution
(2) 0.1 ml of streptokinase+0.2 ml of plasminogen+0.7 ml of physiological sodium chloride solution
(3) 0.1 ml of streptokinase+0.3 ml of plasminogen+0.6 ml of physiological sodium chloride solution
(4) 0.1 ml of streptokinase+0.4 ml of plasminogen+0.5 ml of physiological sodium chloride solution
(5) 0.1 ml of streptokinase+0.5 ml of plasminogen+0.4 ml of physiological sodium chloride Table 1

| | | Data complied from patents undergoing activator treatment | | | | |
|---|---|---|---|---|---|---|
| | | | | Ankle pressure (mm Hg) | | Period of time until first signs |
| Ref. no. | Age (years) | Location | Length of stenoses | prior to therapy | after therapy | of widening were recorded |
| 01 | 61 | Right comm. iliac stenosis | 10 mm | 80 | 150 | 24 hours |
| 02 | 54 | Left Ext. iliac stenosis | 8 mm | 80 | 140 | 24 hours |
| 03 | 55 | Left comm. iliac stenosis | 7 mm | 90 | 110 | 24 hours |
| 04 | 72 | Right ext. iliac stenosis +femoral occlusion | 5 mm | 62 | 112 | 24 hours |

4 iliac stenoses of the irregular, crumbly type known to respond favorably to lytic therapy were treated with activator infusions. In one case (Ref. No. 04) a femoral occlusion was present on the equilateral side.

A definite rise in post-stenotic pressure by 32 mm Hg was recorded in all of the 4 patients 24 hours after start of activator therapy. This proved conclusively thrombolytic effect of activator therapy.

solution
(6) 0.1 ml of streptokinase+0.6 ml of plasminogen+0.3 ml of physiological sodium chloride solution.

For testing the precipitability by means of streptokinase antiserum, the mixtures were examined by immuni-electrophoresis at pH 8.6. For this purpose, the mixtures were allowed to react with antiserum against streptokinase. The free streptokinase contained in the mixture formed a precipitate with the homologous antibody. As the concentration of plasminogen increased, the precipitability decreased until there was no more precipitate in batch (5) containing streptokinase and human plasminogen in a weight ratio of 1:2.5 (corresponding to a molar ratio of about 1:1.4.)

In a test on animals, the reduced reactivity with the homologous antibody could also be established:

10 Guinea pigs were immunized by a single subcutaneous injection of 0.5 ml of a 0.2% streptokinase solution. 21 days later, intravenous injections were made on 5 animals using 0.5 ml of the 0.2% streptokinase solution and on the other 5 animals using 0.5 ml of the preparation of the invention, containing streptokinase and plasminogen in a ratio of 1:2.5.

None of the animals to which the preparation of the invention had been injected showed any reaction. In contradistinction thereto, all guinea pigs which had been immunized with streptokinase and given an injection after 21 days suffered from a shock. Three thereof died.

19 Guinea pigs were subcutaneously immunized by means of the preparation of the invention containing streptokinase and plasminogen in a ratio of 1:2.5. After 21 days, intravenous injections were made on 9 animals using the preparation of the invention employed for the immunization and on the other 10 animals using 0.5 ml of 0.2% streptokinase along.

All animals which had been boostered with the preparation of the invention suffered from a shock. Five animals thereof died. The ten animals, however, to which streptokinase alone had been injected, survived. Only one animal thereof showed a slight shock effect. This is evidence of the fact that the antigenicity of the preparation of the invention and its property of producing antibodies are reduced to a large extent or even eliminated.

We claim:

1. A method for the treatment of thromboembolisms in a patient, said method consisting essentially of intravenously administering to said patient an effective amount of a complex formed between streptokinase and plasminogen in a mol ratio from 2:1 to 1:2 in combination with a physiologically tolerable aqueous liquid diluent.

2. The method of claim 1 wherein said complex is formed between streptokinase and plasminogen in an approximate 1:1 mol ratio.